// 
US011918714B2

(12) United States Patent
Hsu-Luk et al.

(10) Patent No.: US 11,918,714 B2
(45) Date of Patent: Mar. 5, 2024

(54) UVC GERMICIDAL LIGHTING WITH SENSOR AND RELAY FOR SAFETY

(71) Applicant: Denovo Lighting, LLC, Flushing, NY (US)

(72) Inventors: Georgiana Hsu-Luk, Flushing, NY (US); Danielle Luk, Flushing, NY (US)

(73) Assignee: Denovo Lighting, LLC, Flushing, NY (US)

( * ) Notice: Subject to any disclaimer, the term of this patent is extended or adjusted under 35 U.S.C. 154(b) by 431 days.

(21) Appl. No.: 16/920,651

(22) Filed: Jul. 3, 2020

(65) Prior Publication Data

US 2020/0330638 A1 Oct. 22, 2020

Related U.S. Application Data

(60) Provisional application No. 63/042,048, filed on Jun. 22, 2020.

(51) Int. Cl.
*A61L 9/20* (2006.01)
*H05B 47/115* (2020.01)

(52) U.S. Cl.
CPC ............ *A61L 9/20* (2013.01); *H05B 47/115* (2020.01); *A61L 2209/111* (2013.01); *A61L 2209/12* (2013.01)

(58) Field of Classification Search
CPC ..................................... A61L 9/20; A61L 2/10
See application file for complete search history.

(56) References Cited

U.S. PATENT DOCUMENTS

| 5,668,446 | A | 9/1997 | Baker |
| 8,859,994 | B2 | 10/2014 | Deal |
| 9,666,424 | B1 | 5/2017 | Veloz et al. |
| 9,861,239 | B1* | 1/2018 | Robinson ............. A47K 13/302 |
| 10,299,342 | B1* | 5/2019 | Reddy .................. H05B 47/175 |
| 2008/0008620 | A1* | 1/2008 | Alexiadis .................. F21S 4/26 |
| | | | 422/186.3 |
| 2009/0004066 | A1* | 1/2009 | Cheng ..................... A61L 9/205 |
| | | | 422/120 |

(Continued)

FOREIGN PATENT DOCUMENTS

| CN | 201892068 U | 7/2011 |
| CN | 201892068 U | 7/2011 |

(Continued)

*Primary Examiner* — Kevin Joyner
(74) *Attorney, Agent, or Firm* — Fox Rothschild LLP; Carol E. Thorstad-Forsyth

(57) ABSTRACT

The present invention is directed to a device consisting of at least one occupancy sensor and relay switch for providing power to UVC germicidal light sources when the at least one sensor does detect the absence of a person or object in the room or space, and automatically turns off the UVC germicidal light sources when the at least one sensor does detect the presence of a person or object entering or already in a room or space. Additionally, the same device using the at least one sensor and relay switch can include general lighting white color light sources that energize automatically when the at least one sensor does detect the presence of a person or object in a room or space, and automatically turns off the general lighting white color light sources when the at least one sensor does detect the absence of a person or object in the room or space.

58 Claims, 7 Drawing Sheets

(56) References Cited

U.S. PATENT DOCUMENTS

2012/0126134 A1* 5/2012 Deal ..................... G01J 1/429
  250/372
2016/0375163 A1* 12/2016 Hawkins ............. F21V 33/0068
  422/22

FOREIGN PATENT DOCUMENTS

| CN | 203298034 U | 11/2013 |
| CN | 203298034 U | 11/2013 |
| CN | 203477954 U | 3/2014 |
| CN | 203477954 U | 3/2014 |
| WO | 2013/189012 A1 | 12/2013 |
| WO | 2013189012 | 12/2013 |

* cited by examiner

UVC GERMICIDAL LIGHTING WITH SENSOR AND RELAY FOR SAFETY

PRIORITY APPLICATION

This present application claims the benefits and earlier filing date of Provisional Patent Application No. 63/042,048 filed on Jun. 22, 2020 under the same invention title.

FIELD OF THE INVENTION

The present invention relates to a device for controlling the illumination in a room or space using at least one sensor and a relay switch. The device can be used with UVC germicidal lamps that energize automatically when the at least one sensor detects the absence of a person or object in the room or space, and automatically turns off the UVC germicidal lamps when the at least one sensor detects the presence of a person or object in the room or space. Additionally, the same device can include white color general lighting lamps that energize automatically when the at least one sensor detects the presence of a person or object in the room or space, and automatically turns off the white color general lighting lamps when the at least one sensor detects the absence of a person or object in the room or space while using the at least one sensor and relay switch in the same device.

BACKGROUND OF THE INVENTION

The novel coronavirus (COVID-19) has changed society immeasurably, and in the process, impacted technology and product development in profound ways. The research and technology communities are looking for ways to prevent and mitigate the present pandemic, minimize possible resurgence of the present pandemic, and help prevent future outbreaks and pandemics by using UVC-band fluorescent lighting and solid-state lighting (SSL) technology as tools to disinfect surfaces and deactivate viruses in the air including the coronavirus. Still UVC can also be a hazard for humans and must be applied carefully with research backing the application. In this pandemic-driven time, some companies are trying to rush the technology to market in unsafe and unproven forms. UVC lamps and LEDs may prove invaluable in germicidal and sterilizing applications, but the industry must get the applications correct and make it safe for the general public to use and implement in their own rooms and spaces.

UVC lamps and UVC type LEDs fall in the wavelength range from 100 nm to 280 nm. Traditionally, UVC germicidal and sterilizing was performed using 254 nm wavelength UVC lamps either in fluorescent tubes or HID type lamps using ballasts, and cold cathode lamps with inverters. For safety, the UVC lamps were used on timers, or were turned on and off using a manual power switch, or were automated with control by a remote computer. More recently, UV LED manufacturers are developing and manufacturing UVC LEDs with wavelengths in the range from 250 nm to 280 nm for specific germicidal and sterilizing applications. There is a definite need for an automatic safety device to turn off the potentially harmful UVC germicidal lamps and lighting fixtures when a person or object enters a room or space.

Presently, occupancy sensors are used as energy savings devices. They operate by turning on lighting when a person or object enters a room or space, and turns off the lighting when a person or object exits the room or space after a set hold time. This method of operation is opposite to what needs to be done for the safe use of UVC germicidal lamps and lighting fixtures. The present invention overcomes these drawbacks and provides many other advantages and improvements.

For primarily energy savings purposes, there are many patents that use motion sensors and/or light sensors to operate general lighting fixtures and lamps. Some use the sensors remotely while some use the sensors internal to the lighting fixtures. The various embodiments of the present invention use a reverse operation relay switch to turn on and off UVC lighting device either in solo or in combination with general lighting devices.

For example, U.S. Pat. No. 5,668,446 issued to Baker on Sep. 16, 1997 entitled, "Energy Management Control System for Fluorescent Lighting discloses an energy saving lighting control system for operating fluorescent light fixtures with means for controlling the light level base on the inputs from light sensors. Likewise, World Patent Number WO2013189012 published on Dec. 27, 2013 entitled, "Lighting control device for LED and fluorescent lamp" discloses an arrangement of electric circuit elements in a lighting control device that are activated by means of a human body motion detector and illumination sensor for detecting the proximity and presence or movement of a person or object. China Patent Number CN201892068U granted on 07-06-2011 entitled, "Microwave sensitive LED lamp tube" discloses an energy saving general lighting LED lamp tube with automatic control by a microwave sensor. And also, China Patent Number CN203477954U granted on 03-12-2014 entitled, "Gradually-changing-type dimming LED fluorescent lamp controlled by pyroelectric infrared intelligent sensor" discloses a dimmable energy saving LED fluorescent lamp controlled by a pyroelectric infrared or PIR intelligent sensor.

For UV germicidal and sterilizing lighting fixtures and lamps, there are some patents that use remote sensors including motion or light sensors in solo or in combination to control the UV lighting. While others use other methods of control including remote computers to turn the UV devices on and off. In contrast, the occupancy sensors operate in solo without the use of light sensors with a relay switch both of which are mounted in the UVC germicidal lighting devices and/or general lighting devices.

U.S. Pat. No. 8,859,994 issued to Deal on Oct. 14, 2014 entitled, "Disinfection Device and Method" discloses a UV-C are sterilizer or disinfector incorporated into a building structure with remote radiation and motion sensors to monitor the amount of ultra-violet radiation emitted in a room of the building for safety.

U.S. Pat. No. 9,666,424 issued to Veloz et al. on May 30, 2017 entitled, "Method and apparatus for operating a germicidal UV Device with a Programmable Logic Controller and a Bluetooth Low Energy Solution" employs a programmable logic controller or computer with wireless Bluetooth communications to remotely operate germicidal UV devices.

Lastly, China Patent Number CN203298034U granted on 11-20-2013 entitled, "Light emitting diode (LED) lighting germicidal lamp" discloses a kind of LED illumination and UV sterilization integrate lamp in one. The LED illumination or the UV sterilization light sources can be turned on independently or each other, or both the LED illumination and the UV sterilization light sources can be turned on simultaneously. In contrast, the present invention can turn on one or the other lighting, but not both on together at the same time.

Based on the above disclosures, it is an objective of the present invention to provide a safety device and system to automatically turn off UVC germicidal lighting when a person or object comes near the UVC germicidal lighting, and to automatically turn on UVC germicidal lighting when a person or object moves away from the UVC germicidal lighting by using at least one occupancy sensor and relay switch.

Another object of the present invention is to provide a device and system to automatically turn on white color general lighting when a person or object comes near the white color general lighting, and to automatically turn off the white color general lighting when a person or object moves away from the white color general lighting by using at least one occupancy sensor and relay switch.

Yet another object of the present invention is to provide a safety device and system to automatically turn off UVC germicidal lighting and at the same time, turn on white color general lighting when a person or object comes near the combination dual UVC germicidal lighting and white color general lighting, and to automatically turn on UVC germicidal lighting and at the same time, turn off the white color general lighting when a person or object moves away from the combination dual UVC germicidal and white color general lighting by using the same at least one occupancy sensor and relay switch.

Also, another object of the present invention is to provide a UVC germicidal device that is more efficient than using portable UVC germicidal device options.

And yet another object of the present invention is to provide both a combination dual UVC germicidal lighting and white color general lighting device that can be easily retrofitted into new and existing transportation vehicles including buses, trains, and boats.

A final object of the present invention is to provide a combination dual UVC germicidal lighting and white color general lighting device that can continuously operate at all times with no downtime and no additional labor as long as there is power available.

SUMMARY OF THE INVENTION

The present invention relates to a combination sensor and relay switch UVC light source for irradiating a room or space with germicidal UVC wavelengths of light to disinfect and sterilize the room or space when no one is present in said room or space. The UVC light source turns on automatically after a preset time when the sensor detects the room or space is empty, and will automatically turn off when the sensor detects someone is entering or is in the room or space to prevent the UVC wavelengths of light to cause damage to a person or persons entering or is presently in the room or space. The sensor continuously monitors the room or space for the presence of a person or objects in the room or space and will keep the UVC light source disabled until the person or persons should leave the space after a preset period of time that can be set on the sensor itself.

The subject invention serves as an automatic safety switch to turn off the UVC light source and UVC wavelengths of light whenever someone is entering or is still in the room or space where the sensor and UVC light source is installed.

In addition to just providing power to UVC light sources, the same device using the same sensor and relay switch can also power general lighting light sources that energize automatically when the sensor detects the presence of a person or object in the room or space, and turns off the general lighting lamps when the sensor senses the absence of a person or object in the room or space. This allows the use of one fixture with multiple light sources including UVC wavelengths of light in combination with general lighting full spectrum wavelengths of white color light sources for use together in a room or space.

At times, a single occupancy sensor is not enough for the accurate detection of an object or person in a room or space with the single sensor sometimes providing false alarms or not detecting properly. To overcome this problem, the various embodiments of the present invention can use more than one sensor or more than one type of sensor for detection. The at least one sensor can be of the same type and variety, but mounted in different locations for better coverage or a mixture of different types of sensors and technologies may be used for optimum detection. Or, there can be a mixture of different types of sensors and quantity of sensors used for best performance. For example, the present embodiments can use a combination dual technology PIR and a microwave sensor together either in solo packages or combined into one single package. Therefore, any combination and number of sensors and types of sensors may be used in any of the embodiments of the present invention.

The present devices will operate the UVC germicidal lighting in solo or in combination with white color general lighting when both sensors detect an object or person in a room or space at the same time, or when any one of the sensors are activated. The PIR section operates by detecting a rapid change in temperature when a person crosses a protected area. When a beam experiences a change in heat (projected back through the lens), a pulse is generated by the sensor element. The microwave transmitter sends out short bursts of RF energy, and the receiver detects changes in the returned signal caused by motion within its coverage area. The microwave sensor is unaffected by visible light, air drafts, or temperature changes (as from space heaters or air conditioners, for example), but is sensitive to motion. Strong vibrations can be troublesome. Microwave signals may pass through non-metallic walls and windows. Infrared is virtually unaffected by vibration, and will not penetrate walls or windows. Thus, the two complementary technologies will provide an inherent immunity to false alarms when both the PIR sensor and microwave sensor are activated at the same time. Dual technology is ideal for use in hostile environments. Since both must trip simultaneously to cause an alarm, installation is easier and requires less discipline.

One embodiment of the present invention uses at least one occupancy sensor with a Normally Closed (NC) Single Pole Single Throw (SPST) AC-to-AC power relay switch to reverse the operation of the normal operation of at least one occupancy sensor. The AC-to-AC relay switch will turn off the UVC germicidal lighting when a person or object enters a space, and turns back on the germicidal lighting when a person or object exits the space after a set hold time. This relay switch can be implemented into new or existing germicidal fixtures that use UVC fluorescent or HID lamps and ballasts, or cold cathode lamps with inverters. This allows for the safe operation of separate and dedicated UVC germicidal lighting fixtures only.

In some applications, there may not be enough room in a space to install both general lighting for illumination and then to add dedicated UVC germicidal lighting as well. In addition, the installation of separate and dedicated UVC germicidal lighting may require additional power circuits to be installed and connected to the fixtures, which will add installation and possible construction charges for the new installation. For this reason, another embodiment of the present invention uses at least one occupancy sensor with an AC-to-AC power relay switch to control both UVC germicidal and general lighting in the same luminaire. In this embodiment, at least one occupancy sensor is used with a Normally Closed (NC) and Normally Open (NO) Single Pole Double Throw (SPDT) AC-to-AC power relay switch to alternately turn on and off power to separate UVC germicidal and general lighting. This AC-to-AC relay switch can be implemented into new or existing lighting fixtures that use UVC fluorescent or HID lamps with dedicated ballasts or cold cathode lamps with inverters, and general lighting fluorescent or HID lamps with their own separate and dedicated ballasts.

Yet another embodiment of the present invention uses at least one occupancy sensor with a Normally Closed (NC) Single Pole Double Throw (SPDT) DC-to-AC power relay switch to reverse the operation of the normal operation of at least one occupancy sensor installed in a lighting device to power dedicated UVC LEDs. The DC-to-AC relay switch will turn off the UVC LEDs when a person or object enters a space, and turns back on the UVC LEDs when a person or object exits the space after a set hold time. This retrofit UVC LED germicidal lighting device can be installed into new and existing lighting fixtures that use conventional fluorescent or HID lamps and ballasts, and cold cathode lamps with inverters to easily convert them into safe and dedicated UVC LED germicidal and sterilization lighting.

Also, in some applications like in a public transportation vehicle bus, train, or boat, and in some tunnel lighting that use existing fluorescent ballast type fixtures, there may not be enough room or a budget to install additional dedicated UVC germicidal lighting to their existing general lighting. For example, the MTA of New York has spent about $1 million to purchase 150 UVC portable lamps from a startup company named PURO and begun the first phase of the experimental program in hopes of eradicating the coronavirus from its fleet of subway trains and buses. However, the rather large portable UVC lamps on wheels are moved from car to car at the bus stops or train depot after about 30 minutes of irradiation times. This method is time consuming, very laborious, and not efficient. For this reason, this embodiment of the present invention uses an integral at least one occupancy sensor and integral DC-to-AC power relay switch to control both UVC germicidal and general lighting in the same lighting device. The UVC germicidal lamps and general lighting are used in existing light fixtures already installed in the buses and subway trains to work automatically to sterilize the vehicles when no one is present and provide general lighting when there are occupants in the bus or subway train spaces. Since transportation vehicles including buses, trains, and boats operate on primarily 12 VDC battery power for the lighting, a properly rated inverter to convert the low voltage 12 VDC powered light fixtures to operate the high-voltage 120 VAC lamps of the present embodiment. Besides 12 VDC, other low voltages including 24 VDC and 48 VDC may be supplied in the transportation vehicles, and as mentioned before, the UVC germicidal lamps of the present embodiment may operate at other high voltages including 220 VAC and 277 VAC, etc. and not just on 120 VAC power.

In this embodiment, an at least one occupancy sensor is used with a Normally Closed (NC) and Normally Open (NO) Single Pole Double Throw (SPDT) DC-to-AC power relay switch to alternately turn on and off power to separate UVC LED germicidal and white color general lighting type LEDs in the same lighting device. This retrofit combination UVC LED germicidal and white color general lighting type LED lighting device each with their respective and separate built-in LED drivers can be installed into new and existing lighting fixtures that use conventional fluorescent or HID lamps and ballasts, and cold cathode lamps with inverters, or ballast bypass line voltage for power to easily convert them into combination UVC LED germicidal and white color general lighting type LED lighting.

In a final embodiment, the inverter is not needed and the UVC LED lamps are powered directly on DC power as provided in most transportation vehicles including buses, trains, and boats. In this embodiment, an at least one occupancy sensor is used with a Normally Closed (NC) and Normally Open (NO) Single Pole Double Throw (SPDT) DC-to-DC power relay switch to alternately turn on and off power to separate UVC LEDs in solo or in alternate combination with white color general lighting type LEDs. This retrofit combination UVC LEDs in solo or in alternate combination with white color general lighting type LED lighting device each have respective and separate built-in LED drivers can be installed into new and existing lighting fixtures that use conventional fluorescent or HID lamps and ballasts, and cold cathode lamps with inverters, or ballast bypass line voltage for power to easily convert them into combination UVC LED germicidal lighting with optional white color LED general lighting.

These and other aspects, features, and advantages of the present invention will become more readily apparent from the following attached drawings and the detailed description of the preferred embodiments.

BRIEF DESCRIPTION OF THE DRAWINGS

The preferred embodiments of the invention will be described in conjunction with the appended drawings provided to illustrate and not to limit the invention, where like designations denote like elements and in which.

DETAILED DESCRIPTION

Figure 1:
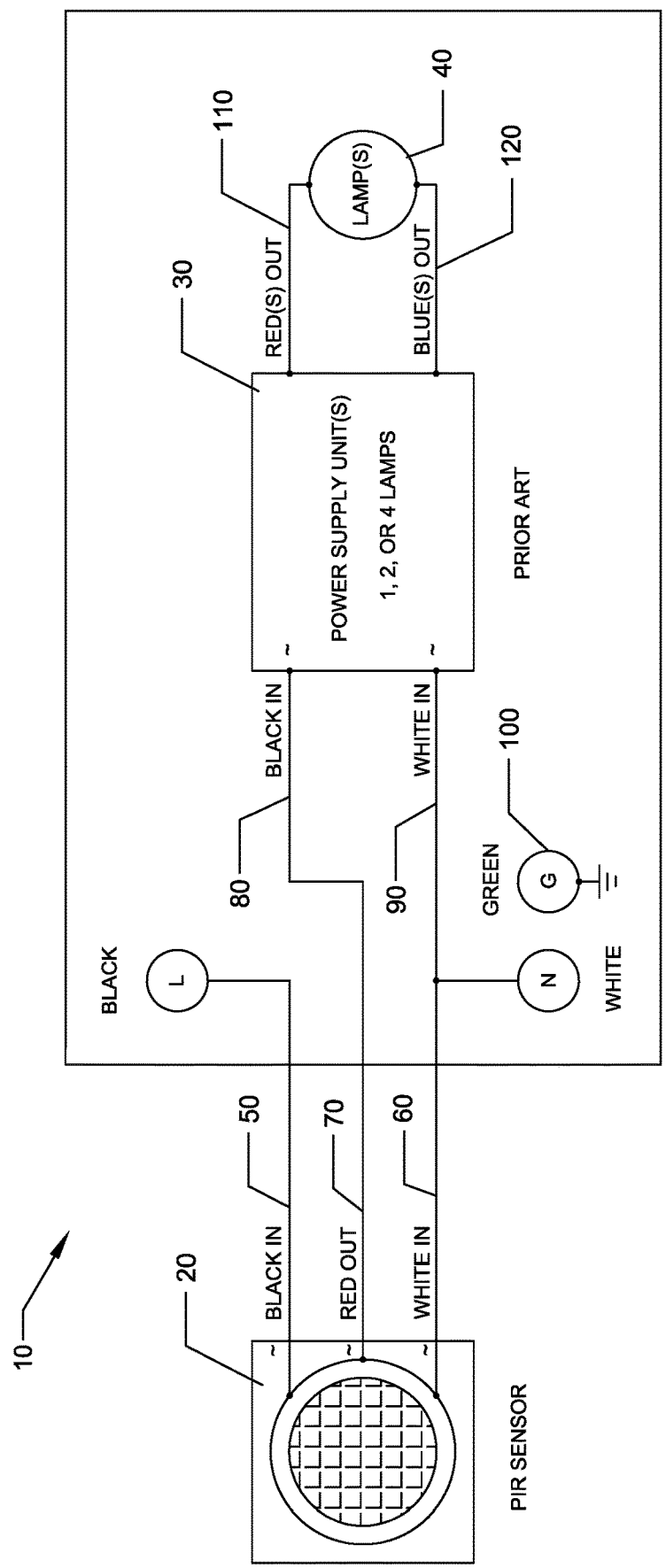
FIG. 1 is a view of a prior art luminaire showing a schematic wiring diagram of an occupancy sensor connected to at least one power supply unit for providing power to at least one light source lamp.

FIG. 1 is a view of a prior art luminaire 10 showing a schematic wiring diagram of an occupancy sensor 20 connected to at least one power supply unit 30 for providing power to at least one light source lamp 40. The sensor 20 shown here in FIG. 1 is a PIR or Passive Infrared occupancy sensor 20. Other types of motion sensors may be used here including microwave, ultrasound, radio-frequency, radar, etc. either in solo or in combination with any other type of motion sensor (not shown). The PIR sensor 20 is a high-voltage AC device for operation with 120Vac, 60 Hz power. Other voltages including 220Vac or 277Vac, etc. may be used depending on the mains utility power service available in the installation site. An input line HOT black color wire 50 and common NEUTRAL white color wire 60 are connected to 120Vac to the PIR sensor 20. The LOAD output red color wire 70 is connected to the line HOT black wire 80 of the power supply unit 30, and the common NEUTRAL white color wire 60 is connected to the common NEUTRAL white color wire 90 of the power supply unit 30. The green color wire 100 is ground and connected to AC Ground back to the main utility circuit breaker panel. The power supply unit 30 may be a fluorescent ballast to power at least one fluorescent lamp, a HID ballast to power at least one HID lamp, an inverter to power a cold cathode lamp, or an LED driver to power at least one LED lamp using the RED color output wires 110 and BLUE color output wires 120 exiting from the power supply unit 30.

In normal operation, when a person or object (not shown) enters the room or space where this luminaire is installed, the PIR sensor 20 will output a high-voltage 120Vac signal on the LOAD output red color wire 70 to power on the power supply unit 30 and turn on the lamp(s) 40. After a preset HOLD time to prevent false triggering and when the PIR sensor 20 does not sense the presence of a person or object (not shown) in the room or space and after the person (not shown) has exited the room or space (not shown), the PIR sensor 20 will stop sending a high-voltage 120Vac signal to the LOAD output red color wire 70 to turn off the power to the lamp(s) 40. This method of operation helps to conserve energy by turning off the lamp(s) 40 when no one is in the room or space to save energy.

Figure 2:
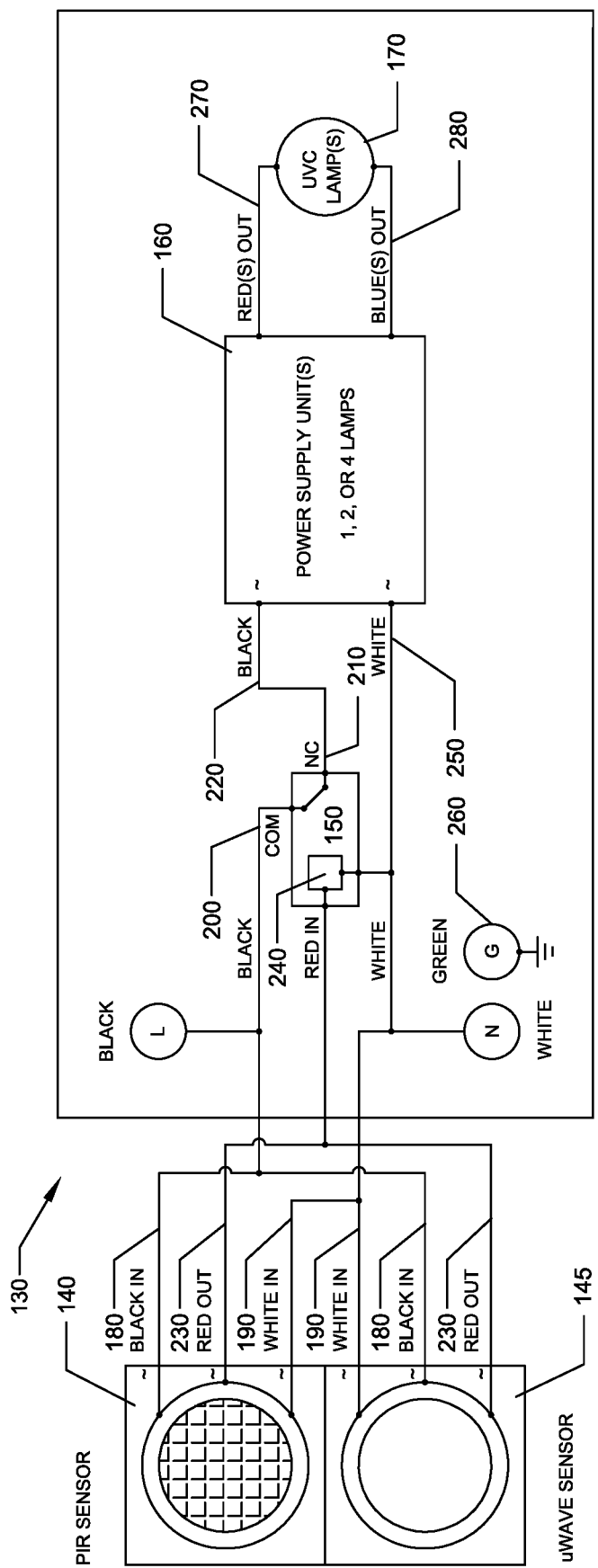
FIG. 2 is a view of a germicidal luminaire showing a schematic wiring diagram of a first embodiment of the present invention including at least one occupancy sensor connected to an AC-to-AC relay switch, and then connected to at least one power supply unit for providing power to at least one UVC light source lamp.

FIG. 2 is a view of a UVC germicidal luminaire 130 showing a schematic wiring diagram of a first embodiment of the present invention including sensors 140, 145 connected to an AC-to-AC relay switch 150, and then connected to at least one power supply unit 160 for providing power to at least one UVC light source lamp 170. The relay switch 150 can be an electro-magnetic, solid-state (SSR), electronic, mechanical, low-voltage reed, or other type of relay. Sensor 140 shown here in FIG. 2 is a PIR or Passive Infrared occupancy type sensor 140, and sensor 145 is a microwave type sensor 145. Additional types of motion sensors may be used here including PIR, microwave, ultrasound, radio-frequency, radar, etc. (not shown) either in solo or in combination with any other type of motion sensor listed here. PIR sensor 140 and microwave sensor 145 are high-voltage AC devices for operation with 120Vac, 60 Hz power. Other voltages including 220Vac or 277Vac, etc. may be used depending on the mains utility power service available in the installation site. An input line HOT black color wire 180 and common NEUTRAL white color wire 190 is connected to 120Vac to PIR sensor 140 and microwave sensor 145, and also to an AC-to-AC SPST (Single Pole Single Throw) type relay switch 150. The input line HOT black color wire 180 is connected to the COM or Common pin 200 of the relay switch 150, and the NC or Normally Closed pin 210 is connected to the line HOT black wire 220 of the power supply unit 160. Alternatively, the input line HOT black color wire 180 can be connected to the NC or Normally Closed pin 210 of the relay switch 150, and the COM or Common pin 200 is connected to the line HOT black wire 220 of the power supply unit 160 to operate the power supply unit 160 in the same manner. The LOAD output red color wire 230 is connected to the one input end of the AC-to-AC SPST relay switch 150 coil 240 with the second input end of the AC-to-AC SPST relay switch 150 coil 240 connected to the common NEUTRAL white color wires 190. The switched output of AC-to-AC SPST relay switch 150 is connected to the line HOT black wire 220 of the power supply unit 160, and the common NEUTRAL white color wires 190 are connected to the common NEUTRAL white color wire 250 of the power supply unit 160. The green color wire 260 is ground and connected to AC Ground back to the main utility circuit breaker panel. The power supply unit 160 may be a fluorescent ballast to power at least one UVC fluorescent lamp, a HID ballast to power at least one UVC HID lamp, an inverter to power at least one cold cathode lamp, or an LED driver to power at least one UVC LED lamp using the RED color output wires 270 and BLUE color output wires 280 exiting from the power supply unit 160.

In reverse safety operation, when a person or object (not shown) enters the room or space where this germicidal luminaire 130 is installed, PIR sensor 140 and/or microwave sensor 145 will output a high-voltage 120Vac signal on the LOAD red color wire 230 to energize the coil 240 connected between the LOAD red color wire 230 and common NEUTRAL white color wire 190 of the AC-to-AC SPST relay switch 150, thereby disconnecting the NC or Normally Closed connection 210 between COM common 200 and turning off the power supply unit 160 and the lamp(s) 170. After a preset HOLD time to prevent false triggering and when PIR sensor 140 and/or microwave sensor 145 do not sense the presence of a person or object (not shown) in the room or space and after the person (not shown) has exited the room or space (not shown), PIR sensor 140 and/or microwave sensor 145 will stop sending a high-voltage 120Vac signal to the LOAD red color wire 230 to de-energize the coil 240 and to turn back on the power to the UVC germicidal lamp(s) 170 for automatic sterilizing. This method of operation presents an automatic solution to turn off the UVC germicidal lamp(s) 170 and prevent exposure to potentially harmful UVC light when someone enters or is present in the room or space for safety.

Figure 3:
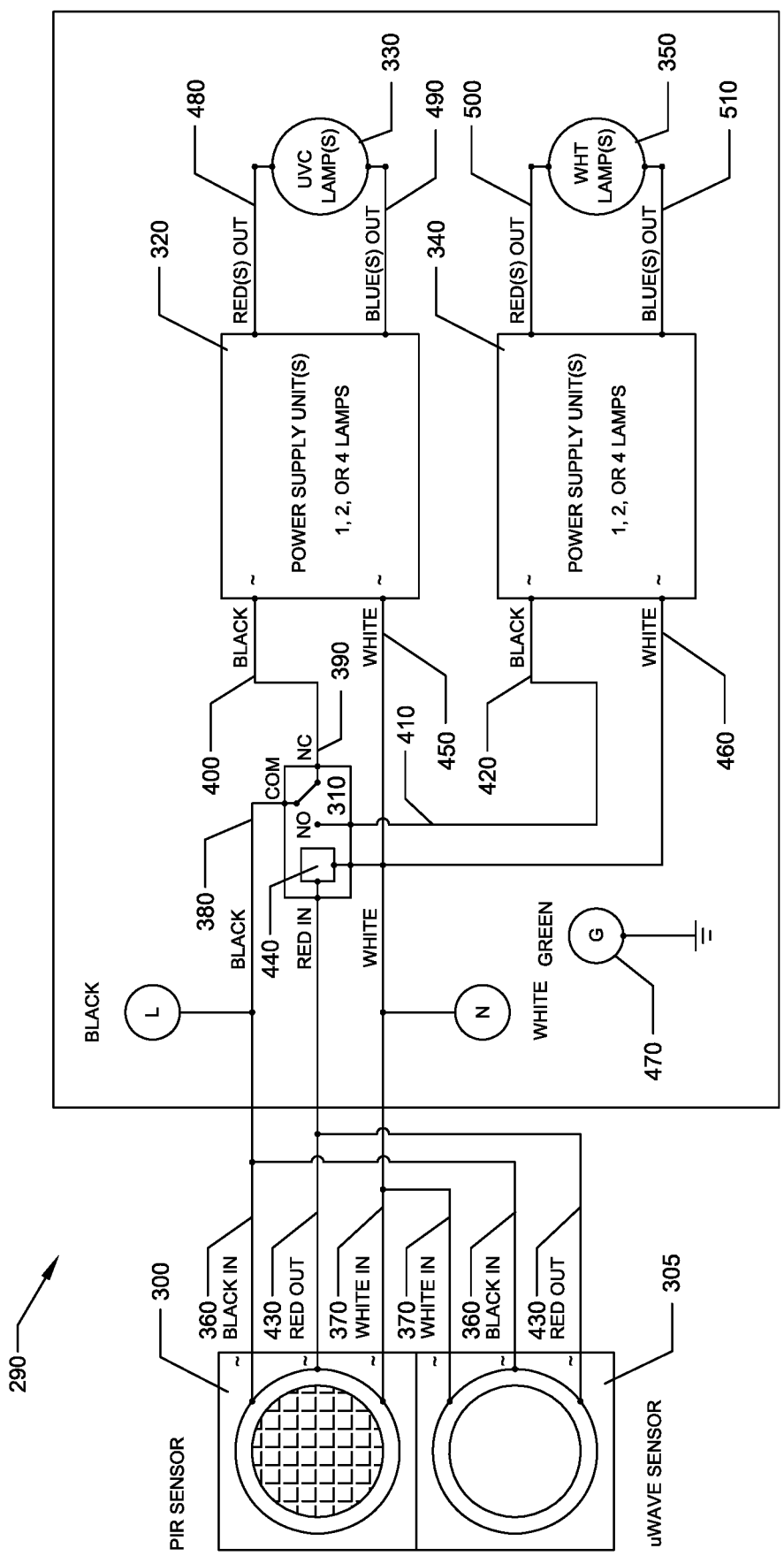
FIG. 3 is a view of a combination germicidal and general lighting luminaire showing a schematic wiring diagram of a second embodiment of the present invention including at least one occupancy sensor connected to an AC-to-AC relay switch connected to a first at least one power supply unit for providing power to at least one UVC light source lamp, and alternately connected to a second at least one power supply unit for providing power to at least one full spectrum white color light source lamp.

FIG. 3 is a view of a combination UVC germicidal and general lighting luminaire 290 showing a schematic wiring diagram of a second embodiment of the present invention including sensors 300, 305 connected to an AC-to-AC Single Pole Double Throw SPDT relay switch 310 connected to a first at least one power supply unit 320 for providing power to at least one UVC light source lamp 330, and alternately connected to a second at least one power supply unit 340 for providing power to at least one full spectrum white color light source lamp 350. The relay switch 310 can be an electro-magnetic, solid-state (SSR), electronic, mechanical, low-voltage reed, or other type of relay. Sensor 300 shown here in FIG. 3 is a PIR or Passive Infrared occupancy type sensor 300, and sensor 305 is a microwave type sensor. Additional types of motion sensors may be used here including PIR, microwave, ultrasound, radio-frequency, radar, etc. (not shown) either in solo or in combination with any other type of motion sensor listed here. PIR sensor 300 and microwave sensor 305 are high-voltage AC devices for operation with 120Vac, 60 Hz power. Other voltages including 220Vac or 277Vac, etc. may be used depending on the mains utility power service available in the installation site. An input line HOT black color wire 360 and common NEUTRAL white color wire 370 is connected to 120Vac to the PIR sensor 300 and microwave sensor 305, and also to an AC-to-AC SPDT (Single Pole Double Throw) type relay switch 310. The input line HOT black color wire 360 is connected to the COM or Common pin 380 of the relay switch 310, and the NC or Normally Closed pin 390 is connected to the line HOT black wire 400 of the first at least one power supply unit 320 that provides power to UVC type germicidal lamps 330 and the NO or Normally Open pin 410 is connected to the line HOT black wire 420 of the second at least one power supply unit 340 that provides power to general lighting full spectrum white color lamps 350. The LOAD output red color wire 430 is connected to the one input end of the AC-to-AC SPDT relay switch 310 coil 440 with the second input end of the AC-to-AC SPDT relay switch 310 coil 440 connected to the common NEUTRAL white color wires 370. The switched output of AC-to-AC SPDT relay switch 310 is connected to the respective line HOT black wires 400, 420 of the at least one power supply units 320, 340 at the corresponding NC 390 and NO 410 outputs from the relay switch 310 that is triggered by the status of the PIR sensor 300 and/or microwave 305 LOAD output red color wire 430 connected to the coil 440 and also connected to the common NEUTRAL white color wires 370. The common NEUTRAL white color wires 370 are all connected together and also to the common NEUTRAL white color wires 450, 460 of the at least one power supply units 320, 340. The green color wire 470 is ground and connected to AC Ground back to the main utility circuit breaker panel. The at least one power supply units 320, 340 may be at least one fluorescent ballast to power at least one UVC fluorescent lamp, at least one HID ballast to power at least one UVC HID lamp, at least one inverter to power at least one cold cathode lamp, or at least one LED driver to power at least one UVC LED lamp each using the RED color output wires 480, 500 and BLUE color output wires 490, 510 exiting from the respective at least one power supply units 320, 340.

In reverse safety operation, when a person or object (not shown) enters the room or space where this combination UVC germicidal and general lighting luminaire 290 is installed, PIR sensor 300 and/or microwave sensor 305 will output a high-voltage 120Vac signal on the LOAD red color wire 430 to energize the coil 440 connected between the LOAD red color wire 430 and common NEUTRAL white color wire 370 of the AC-to-AC SPDT relay switch 310, thereby disconnecting the NC or Normally Closed connection 390 between COM common 380 and turning off the at least one UVC power supply unit 320 and the at least one UVC germicidal lamp 330. After a preset HOLD time to prevent false triggering and when PIR sensor 300 and/or microwave sensor 305 do not sense the presence of a person or object (not shown) in the room or space and after the person (not shown) has exited the room or space (not shown), PIR sensor 300 and/or microwave sensor 305 will stop sending a high-voltage 120Vac signal to the LOAD red color wire 430 to de-energize the coil 440 and to turn back on the power to the at least one UVC germicidal lamp 330 for automatic sterilizing. Alternatively, when a person or object (not shown) enters the room or space where this combination UVC germicidal and general lighting luminaire 290 is installed, PIR sensor 300 and/or microwave sensor 305 will output a high-voltage 120Vac signal on the LOAD red color wire 430 to energize the coil 440 connected between the LOAD red color wire 430 and common NEUTRAL white color wire 370 of the AC-to-AC SPDT relay switch 310, thereby connecting the NO or Normally Open connection 410 between COM common 380 and turning on the at least one general lighting power supply unit 340 and the at least one white color general lighting lamp 350. After a preset HOLD time to prevent false triggering and when PIR sensor 300 and/or microwave sensor 305 do not sense the presence of a person or object (not shown) in the room after the person (not shown) has exited the room or space (not shown), PIR sensor 300 and/or microwave sensor 305 will stop sending a high-voltage 120Vac signal to the LOAD red color wire 430 to de-energize the coil 440 and to turn off the power to the at least one white color general lighting lamp 350. This method of dual operation presents an automatic solution to turn off the UVC germicidal lamps and prevent exposure to potentially harmful UVC light when someone enters or is present in the room or space for personnel safety, and at the same time turning on the general lighting full spectrum white color lighting when someone enters or is still present in the room or space for normal performance and activity by personnel in the room or space (not shown).

Figure 4:
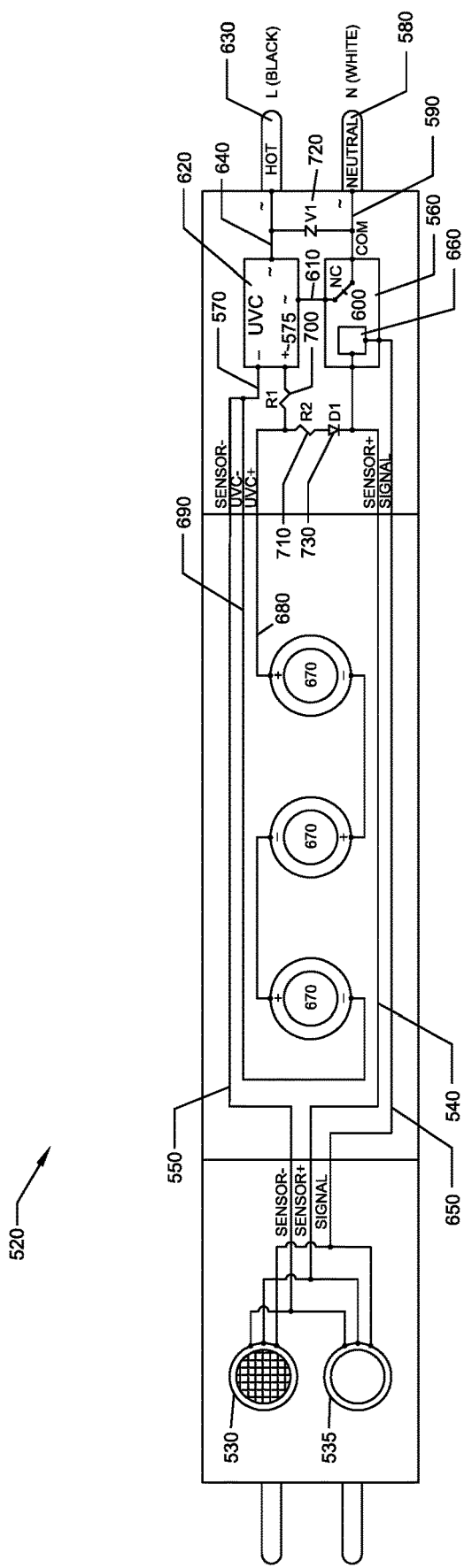
FIG. 4 is a view of a UVC LED germicidal lamp showing a schematic wiring diagram of a third embodiment of the present invention including at least one occupancy sensor connected to a DC-to-AC relay switch, and then connected to at least one LED driver for providing power to at least one UVC LED light source.

FIG. 4 is a view of a UVC LED germicidal lamp 520 showing a schematic wiring diagram of a third embodiment of the present invention including sensors 530, 535 connected to a DC-to-AC relay switch 560, and then connected to at least one UVC LED driver 620 for providing power to at least one UVC LED 670 light source. The relay switch 560 can be an electro-magnetic, solid-state (SSR), electronic, mechanical, low-voltage reed, or any other type of relay.

The UVC LED germicidal lamp 520 represents a conventional fluorescent replacement lamp. The length of the UVC LED germicidal lamp 520 may be 18", 24", 36", 48", or 96" in length, and may be in a T5, T8, or T12 diameter package. Shown in FIG. 4 is a tubular UVC LED lamp 520 with a pair of opposing bi-pins to fit into standard G13 type sockets (not shown). Single opposing pins may also be used to fit into FA8 type sockets, etc., so power will be applied at the two ends in this case (not shown). Also, the lamp can be made in different lamp bases including medium screw E26 and E27, E12 and E14 candelabra, E17 intermediate screw, E39 and E40 mogul, GU23 twist and lock, etc. (not shown). In addition, the UVC LED germicidal lamp 520 may be a Type A replacement lamp to operate with existing ballasts with power applied to non-shunted and shunted sockets; a Type B ballast bypass lamp to work with mains line voltage with AC power applied at one end or at both ends of the lamp; a Type C LED lamp for use with a remote driver with DC input power applied at one end or at both ends of the LED lamp; or a hybrid dual mode Type AB LED lamp for use with a ballast, mains AC power, or DC power applied to one end of both ends of the LED lamp or to any two pins of the LED lamp to energize the LEDs in the UVC LED germicidal lamp 520.

The sensor 530 shown in FIG. 4 is a low-voltage PIR or Passive Infrared occupancy type sensor 530, and sensor 535 is a microwave type sensor 535. Additional types of motion sensors may be used here including PIR, microwave, ultrasound, radio-frequency, radar, etc. (not shown) either in solo or in combination with any other type of motion sensor listed here. PIR sensor 530 and microwave sensor 535 are low-voltage DC devices for operation with 12V DC power. Other voltages including 5Vdc and 24Vdc, etc. may be used depending on the manufacturer and model number of the sensors 530, 535. A 12Vdc input SENSOR+ wire 540 and ground SENSOR− wire 550 is connected to PIR sensor 530 and microwave sensor 535 with the 12Vdc SENSOR+ wire 540 also going to a DC-to-AC SPST (Single Pole Single Throw) type relay switch 560 and the ground SENSOR− wire 550 also going to the UVC LED driver negative output ground 570. A high-voltage NEUTRAL white color power input pin 580 is connected to the COM or Common pin 590 of the relay switch 560, and the NC or Normally Closed pin 600 is connected to the NEUTRAL white color wire 610 of the UVC LED driver 620. Alternatively, the NEUTRAL white color input power pin 580 can be connected to the NC or Normally Closed pin 600 of the relay switch 560, and the COM or Common pin 590 is connected to the NEUTRAL white color wire 610 of the UVC LED driver 620 to operate the UVC LED lamp 520 in the same manner. A high-voltage HOT black color input power pin 630 connects to the HOT driver input black color wire 640 to UVC LED driver 620. Note the line HOT black color input power pin 630 and the NEUTRAL white color input power pin 580 are interchangeable, because the inputs are high-voltage AC and the UVC LED lamp 520 will still operate. A voltage surge protection device V1 720 connected between NEUTRAL white color input power pin 580 and HOT black color input power pin 630 can be a varistor, MOV, etc. to protect the internal circuitry of UVC LED lamp 520 from excessive high voltage surges. The SIGNAL output wire 650 from the PIR sensor 530 and microwave sensor 535 are connected to the one input end of the DC-to-AC SPST relay switch 560 coil 660 with the second input end of the DC-to-AC SPST relay switch 560 coil 660 connected to the PIR sensor 530 and microwave sensor 535 power SENSOR+ 540. PIR sensor 530 and microwave sensor 535 output SIGNAL 650 is a negative sinking voltage that will cause SENSOR+ 540 to energize the coil 660 in the relay switch 560 to turn off the UVC LED driver 620 and thus the UVC LEDs 670 of the UV LED lamp 520. PIR Sensor 530 and microwave sensor 535 SIGNAL 650 may also be a positive sourcing voltage to the coil 660 of DC-to-AC SPST relay switch 560, in which case the other end of the coil 660 will be connected to SENSOR− 550 instead of SENSOR+ 540 to energize the coil 660 in the relay switch 560 to turn off the UVC LED driver 620 and thus the UVC LEDs 670 of the UVC LED lamp 520. The switched output of DC-to-AC SPST relay switch 560 is connected to the NEUTRAL white color wire 610 of the UVC LED driver 620, and the line HOT black color input power pin 630 is connected to the HOT black color wire 640 of the UVC LED driver 620. The UVC LED driver 620 supplies power to the UVC LEDs 670 at positive output UVC+ 680 and negative output UVC− 690. There are three UVC LEDs 670 connected in series in the UVC LED lamp 520 of FIG. 4, but there can more or less UVC LEDs 670 used in the UVC LED germicidal lamp 520 depending on the design and amount of UVC wavelengths of light desired for sterilization from the UVC LED germicidal lamp 520. The UVC LED driver 620 shown in FIG. 4 is a simple full bridge rectifier, but any LED driver may be used including buck converters, boost converters, DC to DC converters, buck-boost drivers, current limiting drivers, constant current drivers, constant voltage drivers, integrated IC driver chips, etc. to provide power to the at least one UVC LED 670 used in the UVC LED germicidal lamp 520 of FIG. 4. Resistors R1 700 and R2 710 are properly selected to produce 12Vdc from UVC LED output voltage UVC+ 680 through diode D1 730 to provide power to PIR sensor 530 and microwave sensor 535 via the SENSOR+ 540 and SENSOR− 550 connections. UVC LED driver positive output 575 connects to resistor R1 700 to provide UVC+ 680 to the UVC LEDs 670. Note that a separate 12Vdc power supply or voltage regulator device or circuit (not shown) may be used to provide 12Vdc power to the PIR sensor 530 and microwave sensor 535. Alternately, some LED drivers provide a 12Vdc auxiliary output for use with sensors (not shown). In addition, PIR sensor 530 and microwave sensor 535 may also be high-voltage type devices and will operate similar to the PIR sensor 140 and microwave sensor 145 described earlier in FIG. 2. Lastly, UVC− 690 and SENSOR− 550 are DC ground for the UVC LED germicidal lamp 520 and are connected to the UVC LED driver negative output ground 570 of UVC LED driver 620.

In reverse safety operation, when a person or object (not shown) enters the room or space where this UVC LED germicidal lamp 520 is installed, PIR sensor 530 and/or microwave sensor 535 will output a negative grounding SIGNAL 650 to energize the coil 660 connected between the positive SENSOR+ connection 540 and negative sinking SIGNAL 650 of the DC-to-AC SPST relay switch 560, thereby disconnecting the NC or Normally Closed connection 600 between NEUTRAL COM 580 and turning off the UVC LED driver 620 and the UVC LED 670 light sources. After a preset HOLD time to prevent false triggering and when PIR sensor 530 and/or microwave sensor 535 do not sense the presence of a person or object (not shown) in the room or space and after the person (not shown) has exited the room or space (not shown), PIR sensor 530 and/or microwave sensor 535 will stop sending a negative sinking SIGNAL 650 to de-energize the coil 660 and will turn back on the power to the UVC LED germicidal lamp 520 for automatic sterilizing. This method of operation presents an automatic solution to turn off the UVC LED germicidal lamp 520 and prevent exposure to potentially harmful UVC light (not shown) when someone enters or is present in the room or space for safety.

Figure 5:
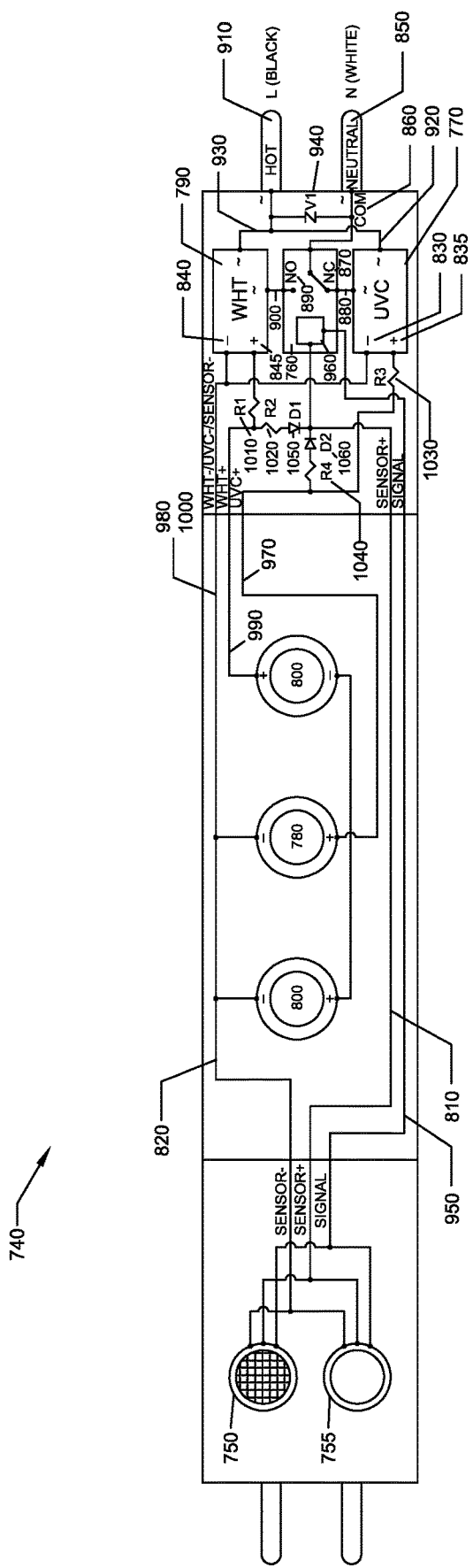
FIG. 5 is a view of a combination UVC germicidal and white color general lighting LED lamp showing a schematic wiring diagram of a fourth embodiment of the present invention including at least one occupancy sensor connected to a DC-to-AC relay switch connected to a first at least one LED driver for providing power to at least one UVC LED light source, and alternately connected to a second at least one LED driver for providing power to at least one full spectrum white color LED light source.

FIG. 5 is a view of a combination UVC germicidal and general lighting lamp 740 showing a schematic wiring diagram of a fourth embodiment of the present invention including sensors 750, 755 connected to a DC-to-AC relay switch 760 connected to a first at least one UVC LED driver 770 for providing power to at least one UVC LED 780 light source, and alternately connected to a second at least one white color general lighting LED driver 790 for providing power to at least one full spectrum white color LED 800 light source. The relay switch 760 can be an electromagnetic, solid-state (SSR), electronic, mechanical, low-voltage reed, or any other type of relay.

The combination UVC germicidal and general lighting LED lamp 740 represents a conventional fluorescent replacement lamp. The length of the combination UVC germicidal and general lighting LED lamp 740 may be 18", 24", 36", 48", or 96" in length, and may be in a T5, T8, or T12 diameter package. Shown in FIG. 5 is a tubular combination UVC germicidal and general lighting LED lamp 740 with a pair of opposing pins to fit into standard G13 type sockets (not shown). Single opposing pins may also be used to fit into FA8 type sockets, etc., so power will be applied at the two ends in this case (not shown). Also, the lamp can be made in different lamp bases including medium screw E26 and E27, E12 and E14 candelabra, E17 intermediate screw, E39 and E40 mogul, GU23 twist and lock, etc. (not shown). In addition, the combination UVC germicidal and general lighting LED lamp 740 may be a Type A replacement lamp to operate with existing ballasts with power applied to non-shunted and shunted sockets; a Type B ballast bypass lamp to work with mains line voltage with AC power applied at one end or at both ends of the lamp; a Type C LED lamp for use with a remote driver with DC input power applied at one end or at both ends of the LED lamp; or a hybrid dual mode Type AB LED lamp for use with a ballast, mains AC power, or DC power applied to one end of both ends of the LED lamp or to any two pins of the LED lamp to energize the LEDs in the combination UVC germicidal and general lighting LED lamp 740.

The sensor 750 shown here in FIG. 5 is a low-voltage PIR or Passive Infrared occupancy type sensor 750, and sensor 755 is a microwave type sensor 755. Additional types of motion sensors may be used here including PIR, microwave, ultrasound, radio-frequency, radar, etc. (not shown) either in solo or in combination with any other type of motion sensor listed here. PIR sensor 750 and microwave sensor 755 are low-voltage DC devices for operation with 12V DC power. Other voltages including 5Vdc and 24Vdc, etc. may be used depending on the manufacturer and model number of the sensors 750, 755. A 12Vdc input SENSOR+ wire 810 and ground SENSOR− wire 820 is connected to the PIR sensor 750 and microwave sensor 755 with the 12Vdc SENSOR+ wire 810 also going to a DC-to-AC SPDT (Single Pole Double Throw) type relay switch 760 and the ground SENSOR− wire 820 also going to the UVC LED driver 770 and white color general lighting LED driver 790 output grounds 830 and 840 respectively. A high-voltage NEUTRAL white color wire 850 from one power input pin of the combination UVC germicidal and general lighting LED lamp 740 is connected to the COM or Common pin 860 of the SPDT relay switch 760, and the NC or Normally Closed pin 870 is connected to the NEUTRAL white wire 880 of the UVC LED driver 790 that provide power to a string of UVC LEDs 780, and the NO or Normally Open pin 890 is connected to the NEUTRAL white wire 900 of the general lighting white light LED driver 790 that provides power to a string of full spectrum white color type LEDs 800. A high-voltage HOT black color wire from a second power input pin 910 of the combination UVC germicidal and general lighting LED lamp 740 is connected to the HOT black wire 920 of the UVC LED driver 770 and also to the HOT black wire 930 of the white color general lighting LED driver 790. Note the line HOT black input power pin 910 and the NEUTRAL white color input power pin 850 are interchangeable, because the inputs are high-voltage AC and the combination UVC germicidal and general lighting LED lamp 740 will still operate. A voltage surge protection device V1 940 connected between power input pins 910, 850 HOT black and NEUTRAL white respectively can be a varistor, MOV, etc. to protect the internal circuitry of combination UVC germicidal and general lighting LED lamp 740 from excessive high voltage surges. The SIGNAL output wire 950 from PIR sensor 750 and microwave sensor 755 are connected to the one input end of the DC-to-AC SPST relay switch 760 coil 960 with the second input end of the DC-to-AC SPST relay switch 760 coil 960 connected to PIR sensor 750 and microwave sensor 755 power SENSOR+ 810. PIR sensor 750 and microwave sensor 755 output SIGNAL 950 is a negative sinking voltage that will cause SENSOR+ 810 to energize the coil 960 in the relay switch 760 to turn off the UVC LED driver 770 and thus the UVC LEDs 780 of the combination UVC germicidal and general lighting LED lamp 740. PIR sensor 750 and microwave sensor 755 SIGNAL 950 may also be a positive sourcing voltage to the coil 960 of DC-to-AC SPST relay switch 760, in which case the other end of the coil 960 will be connected to SENSOR− 820 instead of SENSOR+ 810 to energize the coil 960 in the relay switch 760 to turn off the UVC LED driver 770 and thus the UVC LEDs 780 of the combination UVC germicidal and general lighting LED lamp 740, while appropriately turning on the white color general lighting LED driver 790 and thus the white color LEDs 800 of the same combination UVC germicidal and general lighting LED lamp 740. The switched output of DC-to-AC SPDT relay switch 760 is connected to the respective line NEUTRAL white wires 880, 900 of the UVC LED driver 770 and white color general lighting LED driver 790 at the corresponding NC 870 and NO 890 outputs from the SPDT relay switch 760 that is triggered by the status of the PIR sensor 750 and/or microwave sensor 755. The UVC LED driver 770 supplies power to the UVC LEDs 780 at positive output UVC+ 970 and negative output UVC− 980, and the general lighting white LED driver 790 supplies power to the white color LEDs 800 at positive output WHT+ 990 and negative output WHT− 1000. There is only one UVC LED 780 connected in the combination UVC germicidal and general lighting LED lamp 740 of FIG. 5, but there can be more UVC LEDs 780 used in the UVC germicidal and general lighting LED lamp 740 depending on the design of the UVC LED driver 770 and amount of UVC wavelengths of light desired for sterilization from the combination UVC germicidal and general lighting LED lamp 740. Likewise, there are two white color LEDs 800 connected in series in the combination UVC germicidal and general lighting LED lamp 740 of FIG. 5, but there can be more or less white color LEDs 800 used in the combination UVC germicidal and general lighting LED lamp 740 depending on the design of the white color LED driver 790 and the amount of general lighting output desired to light up a room or space where this combination UVC germicidal and general lighting LED lamp 740 is used.

The UVC LED driver 770 and white color LED driver 790 shown in FIG. 5 are simple full bridge diode rectifiers, but any LED driver may be used including buck converters, boost converters, DC to DC converters, buck-boost drivers, current limiting drivers, constant current drivers, constant voltage drivers, integrated IC driver chips, etc. to provide power to the at least one UVC LED 780 and at least one white color LED 800 used in this combination UVC germicidal and general lighting LED lamp 740 of FIG. 5. Resistors R1 1010, R2 1020, R3 1030, and R4 1040 are properly selected to produce 12Vdc from respective LED output voltages UVC+ 970 and WHT+ 990 through diodes D1 1050 and D2 1060 to provide power to PIR sensor 750 via the SENSOR+ 810 and SENSOR− 820 connections. UVC LED driver positive output 835 connects to resistor R3

1030 to provide UVC+ 970 to at least one UVC LED 780, and white color general lighting LED driver positive output 845 connects to resistor R1 1010 to provide WHT+ 990 to white color LEDs 800. Note that a separate 12Vdc power supply or voltage regulator device or circuit (not shown) may be used to provide 12Vdc power to the PIR sensor 750 and microwave sensor 755. Alternately, some LED drivers provide a 12Vdc auxiliary output for use with sensors (not shown). In addition, PIR sensor 750 and microwave sensor 755 may also be high-voltage type devices and will operate similar to the 120Vac PIR sensor 300 and microwave sensor 305 described earlier in FIG. 3. Lastly, UVC− 980, WHT− 1000, and SENSOR− 820 are all connected together here and serve as the DC ground in this case for the combination UVC germicidal and general lighting LED lamp 740 of this embodiment, but they may be isolated from the each other depending on the circuit design.

In reverse safety operation, when a person or object (not shown) enters the room or space where this combination UVC germicidal and general lighting LED lamp 740 is installed, PIR sensor 750 and/or microwave sensor 755 will output a negative grounding SIGNAL 950 to energize the coil 960 connected between the positive SENSOR+ connection 810 and negative sinking SIGNAL 950 of the DC-to-AC SPDT relay switch 760, thereby disconnecting the NC or Normally Closed connection 870 between NEUTRAL white COM pin 850 to UVC driver NEUTRAL input white wire 880 and turning off the UVC LED driver 770 and the UVC LED 780 light sources. After a preset HOLD time to prevent false triggering and when PIR sensor 750 and/or microwave sensor 755 do not sense the presence of a person or object (not shown) in the room or space and after the person (not shown) has exited the room or space (not shown), PIR sensor 750 and/or microwave sensor 755 will stop sending a negative sinking SIGNAL 950 to de-energize the coil 960 and will turn back on the power to the UVC germicidal LED 780 light sources for automatic sterilizing. Alternatively, when a person or object (not shown) enters the room or space where this combination UVC LED germicidal and general lighting lamp 740 is installed, PIR sensor 750 and/or microwave sensor 755 will send a negative grounding SIGNAL 950 to energize the coil 960 connected between the positive SENSOR+ connection 810 and negative sinking SIGNAL 950 of the DC-to-AC SPDT relay switch 760, thereby connecting the NO or Normally Open connection 890 between NEUTRAL white COM pin 850 to white color general lighting LED driver NEUTRAL input white wire 900 and turning on the at least one white color general lighting LED driver 790 and at least one white color LED 800. After a preset HOLD time to prevent false triggering and when PIR sensor 750 and/or microwave sensor 755 no longer senses the presence of a person or object (not shown) in the room or space and after the person (not shown) has exited the room or space (not shown), PIR sensor 750 and/or 755 will stop sending a negative grounding SIGNAL 950 to the DC-to-AC SPDT relay switch 760 to de-energize the coil 960 and to turn back off the power to the at least one white color LED 800 light source for general lighting. This method of dual operation presents an automatic solution to turn off the UVC germicidal LEDs 780 and prevent exposure to potentially harmful UVC light when someone enters or is present in the room or space for safety, and at the same time turning on the general lighting full spectrum white color LEDs 800 when someone enters or is still present in the room or space for normal performance and activity in the room or space.

Figure 6:
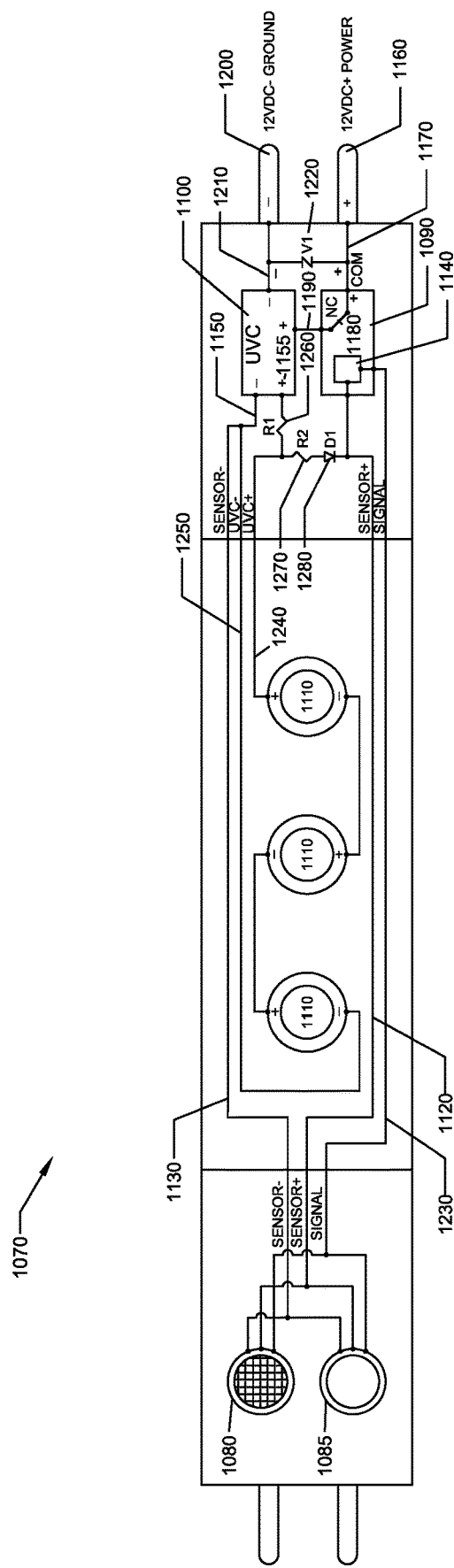
FIG. 6 is a view of a UVC LED germicidal lamp showing a schematic wiring diagram of a fifth embodiment of the present invention including at least one occupancy sensor connected to a DC-to-DC relay switch, and then connected to at least one LED driver for providing power to at least one UVC LED light source.

FIG. 6 is a view of a UVC LED germicidal lamp 1070 showing a schematic wiring diagram of a fifth embodiment of the present invention including sensors 1080, 1085 connected to a DC-to-DC relay switch 1090, and then connected to at least one UVC LED driver 1100 for providing power to at least one UVC LED 1110 light source. The relay switch 1090 can be an electro-magnetic, solid-state (SSR), electronic, mechanical, low-voltage reed, or any other type of relay.

The UVC LED germicidal lamp 1070 represents a conventional fluorescent replacement lamp. The length of the UVC LED germicidal lamp 1070 may be 18", 24", 36", 48", or 96" in length, and may be in a T5, T8, or T12 diameter package. Shown in FIG. 6 is a tubular UVC LED germicidal lamp 1070 with a pair of opposing pins to fit into standard G13 type sockets (not shown). Single opposing pins may also be used to fit into FA8 type sockets, etc., so power will be applied at the two ends in this case (not shown). Also, the lamp can be made in different lamp bases including medium screw E26 and E27, E12 and E14 candelabra, E17 intermediate screw, E39 and E40 mogul, GU23 twist and lock, etc. (not shown). In addition, the UVC LED germicidal lamp 1070 may be a Type A replacement lamp to operate with existing ballasts with power applied to non-shunted and shunted sockets; a Type B ballast bypass lamp to work with mains line voltage with AC power applied at one end or at both ends of the lamp; a Type C LED lamp for use with a remote driver with DC input power applied at one end or at both ends of the LED lamp; or a hybrid dual mode Type AB LED lamp for use with a ballast, mains AC power, or DC power applied to one end of both ends of the LED lamp or to any two pins of the LED lamp to energize the LEDs in the UVC LED germicidal lamp 1070.

The sensor 1080 shown in FIG. 6 is a low-voltage PIR or Passive Infrared occupancy type sensor 1080, and sensor 1085 is a microwave type sensor 1085. Additional types of motion sensors may be used here including PIR, microwave, ultrasound, radio-frequency, radar, etc. (not shown) either in solo or in combination with any other type of motion sensor listed here. PIR sensor 1080 and microwave sensor 1085 are low-voltage DC devices for operation with 12V DC power. Other voltages including 5Vdc and 24Vdc, etc. may be used depending on the manufacturer and model number of sensors 1080, 1085. A 12Vdc input SENSOR+ wire 1120 and ground SENSOR− wire 1130 is connected to PIR sensor 1080 and microwave sensor 1085 with the 12Vdc SENSOR+ wire 1120 also going to a DC-to-DC SPST (Single Pole Single Throw) type relay switch 1090 coil 1140, and the ground SENSOR− wire 1130 also going to the UVC LED driver 1100 LED negative output ground 1150. A low-voltage 12Vdc+ positive input power pin 1160 is connected to the COM or Common pin 1170 of the relay switch 1090, and the NC or Normally Closed pin 1180 is connected to the positive input power wire 1190 of the UVC LED driver 1100. Alternatively, the low-voltage 12Vdc+ positive power input pin 1160 can be connected to the NC or Normally Closed pin 1180 of the relay switch 1090, and the COM or Common pin 1170 is connected to the positive power input wire 1190 of the UVC LED driver 1100 to operate the UVC LED germicidal lamp 1070 in the same manner. Note the low-voltage 12Vdc+ positive input power pin 1160 and 12Vdc− negative input power pin 1200 is interchangeable, as long as they are connected to the corresponding positive and negative power input pins 1160, 1200 respectively to UVC LED driver 1100. A voltage surge protection device V1 1220 connected between power input pins 12Vdc+ 1160 and 12Vdc− 1200 can be a varistor, MOV, etc. to protect the internal circuitry of UVC LED germicidal lamp 1070 from excessive high voltage surges. The SIGNAL output wire 1230 from PIR sensor 1080 and microwave sensor 1085 is connected to the one input end of the DC-to-DC SPST relay switch 1090 coil 1140 with the second input end of the DC-to-DC SPST relay switch 1090 coil 1140 connected to PIR sensor 1080 and microwave sensor 1085 power SENSOR+ 1120. PIR sensor 1080 and microwave sensor 1085 output SIGNAL 1230 is a negative sinking voltage that will cause SENSOR+ 1120 to energize the coil 1140 in the relay switch 1090 to turn off the UVC LED driver 1100 and thus the UVC LEDs 1110 of the UVC LED germicidal lamp 1070. PIR Sensor 1080 and microwave sensor 1085 SIGNAL 1230 may also be a positive sourcing voltage to the coil 1140 of DC-to-DC SPST relay switch 1090, in which case the other end of the coil 1140 will be connected to SENSOR− 1130 instead of SENSOR+ 1120 to energize the coil 1140 in the relay switch 1090 to turn off the UVC LED driver 1100 and thus the UVC LEDs 1110 of the UVC LED germicidal lamp 1070. The switched output of DC-to-DC SPST relay switch 1090 is connected to the positive voltage input wire 1190 of the UVC LED driver 1100, and the negative voltage 12Vdc− negative power input pin 1200 of the UVC LED germicidal lamp 1070 is connected to the negative voltage input wire 1210 of the UVC LED driver 1100 and connecting all negative DC grounds together. The UVC LED driver 1100 supplies power to the UVC LEDs 1110 at positive output UVC+ 1240 and negative output UVC− 1250. There are three UVC LEDs 1110 connected in series in the UVC LED germicidal lamp 1070 of FIG. 6, but there can more or less UVC LEDs 1110 used in the UVC LED germicidal lamp 1070 depending on the design and amount of UVC wavelengths of light desired for sterilization from the UVC LED germicidal lamp 1070. The UVC LED driver 1100 shown in FIG. 6 is a DC to DC converter, but any LED driver may be used including buck converters, boost converters, diode bridge rectifiers, buck-boost drivers, current limiting drivers, constant current drivers, constant voltage drivers, integrated IC driver chips, etc. to provide power to the at least one UVC LED 1110 used in the UVC LED germicidal lamp 1070 of FIG. 6. Resistors R1 1260 and R2 1270 are properly selected to produce 12Vdc from UVC LED output voltage UVC+ 1240 through diode D1 1280 to provide power to PIR sensor 1080 and microwave sensor 1085 via the SENSOR+ 1120 and SENSOR− 1130 connections. UVC LED driver positive output 1155 connects to resistor R1 1260 to provide UVC+ 1240 to UVC LEDs 1110. Note that a separate 12Vdc power supply or voltage regulator device or circuit (not shown) may be used to provide 12Vdc power to the PIR sensor 1080 and microwave sensor 1085. Alternately, some LED drivers provide a 12Vdc auxiliary output for use with sensors (not shown). In addition, PIR sensor 1080 and microwave sensor 1085 may also be high-voltage type devices, and will operate similar to the PIR sensor 140 and microwave sensor 145 described earlier in FIG. 2. In this configuration, the relay switch 1090 will be an AC-to-DC SPDT type device (not shown). Lastly, UVC− 1250 and SENSOR− 1130 are negative DC grounds for the UVC LED germicidal lamp 1070 and are connected to the UVC LED driver negative output ground 1150 of UVC LED driver 1100 and 12Vdc− input power DC ground pin 1200 of UVC LED germicidal lamp 1070.

In reverse safety operation, when a person or object (not shown) enters the room or space where this UVC LED germicidal lamp 1070 is installed, PIR sensor 1080 and/or microwave sensor 1085 will output a negative grounding SIGNAL 1230 to energize the coil 1140 connected between the positive SENSOR+ connection 1120 and negative sinking SIGNAL 1230 of the DC-to-DC SPST relay switch 1090, thereby disconnecting the NC or Normally Closed connection 1180 between NEUTRAL COM 1170 and turning off the UVC LED driver 1100 and the UVC LED 1110 light sources. After a preset HOLD time to prevent false triggering and when PIR sensor 1080 and/or microwave sensor 1085 do not sense the presence of a person or object (not shown) in the room or space and after the person or object (not shown) has exited the room or space (not shown), PIR sensor 1080 and/or microwave sensor 1085 will stop sending a negative sinking SIGNAL 1230 to de-energize the coil 1140 and will turn back on the power to the UVC LEDs 1110 for automatic sterilizing. This method of operation presents an automatic solution to turn off the UVC LED germicidal lamp 1070, and to prevent exposure to potentially harmful UVC light when someone enters or is present in the room or space for personal safety.

Figure 7:
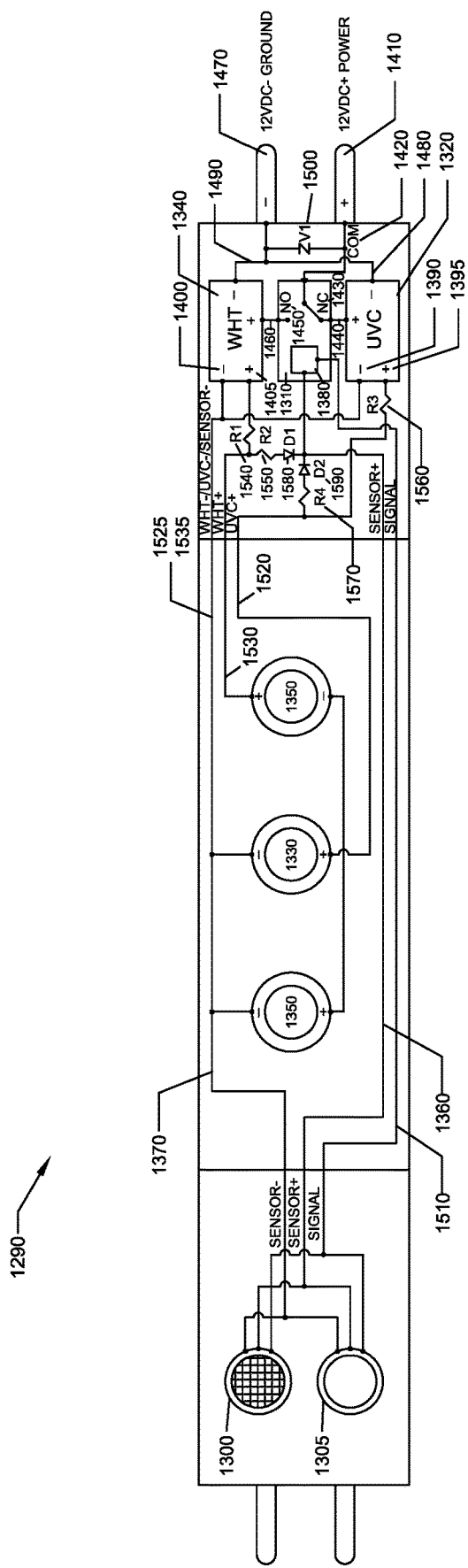
FIG. 7 is a view of a combination UVC germicidal and white color general lighting LED lamp showing a schematic wiring diagram of a sixth and final embodiment of the present invention including at least one occupancy sensor connected to a DC-to-DC relay switch connected to a first at least one LED driver for providing power to at least one UVC LED light source, and alternately connected to a second at least one LED driver for providing power to at least one full spectrum white color LED light source.

FIG. 7 is a view of a combination UVC germicidal and general lighting lamp 1290 showing a schematic wiring diagram of a sixth and final embodiment of the present invention including sensors 1300, 1305 connected to a DC-to-DC relay switch 1310 connected to a first at least one UVC LED driver 1320 for providing power to at least one UVC LED 1330 light source, and alternately connected to a second at least one white color general lighting LED driver 1340 for providing power to at least one full spectrum white color LED 1350 light source. The relay switch 1310 can be an electro-magnetic, solid-state (SSR), electronic, mechanical, low-voltage reed, or any other type of relay.

The combination UVC germicidal and general lighting LED lamp 1290 represents a conventional fluorescent replacement lamp. The length of the combination UVC germicidal and general lighting LED lamp 1290 may be 18", 24", 36", 48", or 96" in length, and may be in a T5, T8, or T12 diameter package. Shown in FIG. 7 is a tubular UVC germicidal and general lighting LED lamp 1290 with a pair of opposing pins to fit into standard G13 type sockets (not shown). Single opposing pins may also be used to fit into FA8 type sockets, etc., so power will be applied at the two ends in this case (not shown). Also, the lamp can be made in different lamp bases including medium screw E26 and E27, E12 and E14 candelabra, E17 intermediate screw, E39 and E40 mogul, GU23 twist and lock, etc. (not shown). In addition, the combination UVC germicidal and general lighting LED lamp 1290 may be a Type A replacement lamp to operate with existing ballasts with power applied to non-shunted and shunted sockets; a Type B ballast bypass lamp to work with mains line voltage with AC power applied at one end or at both ends of the lamp; a Type C LED lamp for use with a remote power supply unit with DC input power applied at one end or at both ends of the LED lamp; or a hybrid dual mode Type AB LED lamp for use with a ballast, mains AC power, or DC power applied to one end of both ends of the LED lamp or to any two pins of the LED lamp to energize the LEDs in the lamp.

The sensor 1300 shown here in FIG. 7 is a low-voltage PIR or Passive Infrared occupancy type sensor 1300, and sensor 1305 is a microwave type sensor 1305. Additional types of motion sensors may be used here including PIR, microwave, ultrasound, radio-frequency, radar, etc. (not shown) either in solo or in combination with any other type of motion sensor listed here. PIR sensor 1300 and microwave sensor 1305 are low-voltage DC devices for operation with 12V DC power. Other voltages including 5Vdc and 24Vdc, etc. may be used depending on the manufacturer and model numbers of sensors 1300, 1305. A 12Vdc input SENSOR+ wire 1360 and ground SENSOR− wire 1370 is connected to PIR sensor 1300 and microwave sensor 1305 with the 12Vdc SENSOR+ wire 1360 also going to a DC-to-DC SPDT (Single Pole Double Throw) type relay switch 1310 coil 1380, and the ground SENSOR− wire 1370 also going to the UVC LED driver 1320 and white color general lighting LED driver 1340 negative output grounds 1390 and 1400 respectively. A low-voltage 12Vdc positive voltage from one power input pin 1410 of the combination UVC germicidal and general lighting LED lamp 1290 is connected to the COM or Common pin 1420 of the SPDT relay switch 1310, and the NC or Normally Closed pin 1430 is connected to the positive power input pin 1440 of UVC LED driver 1320 that provides power to a string of UVC LEDs 1330, and the NO or Normally Open pin 1450 is connected to the positive power input pin 1460 of the general lighting white light LED driver 1340 that provides power to a string of full spectrum white color LEDs 1350. A low-voltage 12Vdc− negative voltage from a second power input pin 1470 of the combination UVC germicidal and general lighting LED lamp 1290 is connected to the negative input voltage wire 1480 of the UVC LED driver 1320, and also to the negative input voltage wire 1490 of the white color general lighting LED driver 1340. Note the low-voltage 12Vdc+ positive input power pin 1410 and 12Vdc− negative input power pin 1470 is interchangeable, as long as they are connected to the corresponding positive and negative power input wires 1440, 1480 of UVC LED driver 1320 and corresponding positive and negative power input wires 1460, 1490 of general lighting white light LED driver 1340. A voltage surge protection device V1 1500 connected between power input pins 12Vdc+ 1410 and 12Vdc− 1470 can be a varistor, MOV, etc. to protect the internal circuitry of combination UV germicidal and general lighting LED lamp 1290 from excessive high voltage surges. The SIGNAL output wire 1510 from PIR sensor 1300 and microwave sensor 1305 is connected to the one input end of the DC-to-DC SPDT relay switch 1310 coil 1380 with the second input end of the DC-to-DC SPDT relay switch 1310 coil 1380 connected to the PIR sensor 1300 and microwave sensor 1305 power SENSOR+ 1360. PIR sensor 1300 and microwave sensor 1305 output SIGNAL 1510 is a negative sinking voltage that will cause SENSOR+ 1360 to energize the coil 1380 in the relay switch 1310 to turn off the UVC LED driver 1320 and thus the UVC LEDs 1330 of combination UVC germicidal and general lighting LED lamp 1290. PIR Sensor 1300 SIGNAL 1510 may also be a positive sourcing voltage to the coil 1380 of DC-to-DC SPDT relay switch 1310, in which case the other end of the coil 1380 will be connected to SENSOR− 1370 instead of SENSOR+ 1360 to energize the coil 1380 in the relay switch 1310 to turn off the UVC LED driver 1320 and thus the UVC LEDs 1330 of the combination UVC germicidal and general lighting LED lamp 1290, while appropriately turning on the white color general lighting LED driver 1340 and thus the white color LEDs 1350 of the same combination UVC germicidal and general lighting LED lamp 1290. The switched output of DC-to-DC SPDT relay switch 1310 is connected to the respective positive input power wires 1440, 1460 of the UVC LED driver 1320 and white color general lighting LED driver 1340 at the corresponding NC 1430 and NO 1450 outputs from the SPDT relay switch 1310 that is triggered by the status of the PIR sensor 1300 and/or microwave sensor 1305. The UVC LED driver 1320 supplies power to the UVC LEDs 1330 at positive output UVC+ 1520 and negative output UVC− 1525, and the general lighting white LED driver 1340 supplies power to the white color LEDs 1350 at positive output WHT+ 1530 and negative output WHT− 1535. There is only one UVC LED 1330 connected in the combination UVC germicidal and general lighting LED lamp 1290 of FIG. 7, but there can be more UVC LEDs 1330 used in the combination UVC germicidal and general lighting LED lamp 1290 depending on the design of the UVC LED driver 1320 and amount of UVC wavelengths of light desired for sterilization from the combination UVC germicidal and general lighting LED lamp 1290. Likewise, there are two white color LEDs 1350 connected in series in the combination UVC germicidal and general lighting LED lamp 1290 of FIG. 7, but there can be more or less white color LEDs 1350 used in the combination UVC germicidal and general lighting LED lamp 1290 depending on the design of the white color LED driver 1340 and the amount of general lighting output illumination desired to light up a room or space where this combination UVC germicidal and general lighting LED lamp 1290 is used.

The UVC LED driver 1320 and white color LED driver 1340 shown in FIG. 7 are simple DC TO DC converters, but any LED driver may be used including buck converters, boost converters, diode bridge rectifiers, buck-boost drivers, current limiting drivers, constant current drivers, constant voltage drivers, integrated IC driver chips, etc. to provide power to the at least one UVC LED 1330 and at least one white color LED 1350 used in this combination UVC germicidal and general lighting LED lamp 1290 of FIG. 7. Resistors R1 1540, R2 1550, R3 1560, and R4 1570 are properly selected to produce 12Vdc from the respective UVC LED output voltages UVC+ 1520 and WHT+ 1530 through diodes D1 1580 and D2 1590 to provide power to PIR sensor 1300 via the SENSOR+ 1360 and SENSOR− 1370 connections. UVC LED driver positive output 1395 connects to resistor R3 1560 to provide UVC+ 1520 to at least one UVC LED 1330, and white color general lighting LED driver positive output 1405 connects to resistor R1 1540 to provide WHT+ 1530 to white color LEDs 1350. Note that a separate 12Vdc power supply or voltage regulator device or circuit (not shown) may be used to provide 12Vdc power to the PIR sensor 1300 and microwave sensor 1305. Alternately, some LED drivers provide a 12Vdc auxiliary output for use with sensors (not shown). In addition, the PIR sensor 1300 and microwave sensor 1305 may also be high-voltage type devices, and will operate similar to the 120Vac PIR sensor 300 and microwave sensor 305 described earlier in FIG. 3. In this configuration, the relay switch 1310 will be an AC-to-DC SPDT type device (not shown). Lastly, UVC− 1525, WHT− 1535, and SENSOR− 1370 are all connected together here and serve as the DC ground in this case for the combination UVC germicidal and white color general lighting LED lamp 1290 of this embodiment, but they may also be isolated from the each other depending on the circuit design.

In reverse safety operation, when a person or object (not shown) enters the room or space where this combination UVC germicidal and general lighting LED lamp 1290 is installed, PIR sensor 1300 and/or microwave sensor 1305 will output a negative grounding SIGNAL 1510 to energize the coil 1380 connected between the positive SENSOR+ 1360 connection and negative sinking SIGNAL 1510 of the DC-to-DC SPDT relay switch 1310, thereby disconnecting the NC or Normally Closed connection 1430 between NEUTRAL white COM 1420 and turning off the UVC LED driver 1320 and the UVC LED 1330 light sources. After a preset HOLD time to prevent false triggering and when PIR sensor 1300 and/or microwave sensor 1305 do not sense the presence of a person or object (not shown) in the room or space and after the person (not shown) has exited the room or space (not shown), PIR sensor 1300 and/or microwave sensor 1305 will stop sending a negative sinking SIGNAL 1510 to de-energize the coil 1380 and will turn back on the power to the UVC LED 1330 light sources for automatic sterilizing. Alternatively, when a person or object (not shown) enters the room or space where this combination UVC LED germicidal and general lighting lamp 1290 is installed, PIR sensor 1300 and/or microwave sensor 1305 will send a negative grounding SIGNAL 1510 to energize the coil 1380 connected between the positive SENSOR+ connection 1360 and negative sinking SIGNAL 1510 of the DC-to-DC SPDT relay switch 1310, thereby connecting the NO or Normally Open connection 1450 between NEUTRAL white COM 1420 and turning on the at least one white color general lighting LED driver 1340 and at least one white color type LED 1350. After a preset HOLD time to prevent false triggering and when PIR sensor 1300 and/or microwave sensor 1305 no longer senses the presence of a person or object (not shown) in the room or space and after the person (not shown) has exited the room or space (not shown), PIR sensor 1300 and/or microwave sensor 1305 will stop sending a negative grounding SIGNAL 1510 to the DC-to-DC SPDT relay switch 1310 to de-energize the coil 1380 and to turn back off the power to the at least one white color general lighting LED driver 1340 and at least one white color type LED 1350 light source for general lighting. This method of dual operation presents an automatic solution to turn off the UVC LEDs 1330 and prevent exposure to potentially harmful UVC light when someone enters or is present in the room or space for safety, and at the same time turning on the general lighting full spectrum white color LEDs 1350 when someone enters or is still present in the room or space for normal performance and activity by personnel in the room or space.

It will be understood that various changes in the details, materials, types, values, and arrangements of the components that have been described and illustrated in order to explain the nature of this invention may be made by those skilled in the art without departing from the principle and scope of the various embodiments of the invention as expressed in the following claims.

What we claim is:

1. A UVC germicidal illumination device, comprising:
a power source configured to supply input power to said UVC germicidal illumination device;
at least one UVC light source configured to generate ultraviolet light;
a first at least one power supply unit configured to provide output power to at least one UVC light source;
a relay comprising a first pin in communication with an input connection of said power source, a second pin in communication with another input connection of said power source, a third pin in communication with an input of said first at least one power supply unit, and fourth pin in communication directly with an output of at least one sensor;
the at least one sensor configured to generate a sensor output signal responsive to a detection of a person or object by the at least one sensor;
wherein said relay is configured to (i) receive, at the fourth pin, the sensor output signal from the at least one sensor and (ii) disconnect the power source from the first at least one power supply unit in response to the received sensor output signal; and
wherein said relay is further configured to re-connect the power source to said first at least one power supply unit when said sensor output signal is no longer being received by the relay.

2. The UVC germicidal illumination device according to claim 1, wherein said power source is AC mains line voltage power source.

3. The UVC germicidal illumination device according to claim 1, wherein said power source is a DC voltage power source.

4. The UVC germicidal illumination device according to claim 1, wherein said first at least one power supply unit is at least one fluorescent ballast.

5. The UVC germicidal illumination device according to claim 1, wherein said first at least one power supply unit is at least one metal halide ballast.

6. The UVC germicidal illumination device according to claim 1, wherein said first at least one power supply unit is at least one inverter.

7. The UVC germicidal illumination device according to claim 1, wherein said first at least one power supply unit is at least one LED driver.

8. The UVC germicidal illumination device according to claim 1, wherein said at least one UVC light source is at least one UVC fluorescent lamp.

9. The UVC germicidal illumination device according to claim 1, wherein said at least one UVC light source is at least one UVC HID lamp.

10. The UVC germicidal illumination device according to claim 1, wherein said at least one UVC light source is at least one UVC cold cathode lamp.

11. The UVC germicidal illumination device according to claim 1, wherein said at least one UVC light source is at least one UVC LED lamp.

12. The UVC germicidal illumination device according to claim 1, wherein said at least one sensor is at least one PIR type sensor.

13. The UVC germicidal illumination device according to claim 1, wherein said at least one sensor is at least one microwave type sensor.

14. The UVC germicidal illumination device according to claim 1, wherein said at least one sensor is at least one radio-frequency type sensor.

15. The UVC germicidal illumination device according to claim 1, wherein said at least one sensor is at least one ultrasonic type sensor.

16. The UVC germicidal illumination device according to claim 1, wherein said at least one sensor is at least one radar type sensor.

17. The UVC germicidal illumination device according to claim 1, wherein said at least one sensor is a combination of at least one PIR type sensor and at least one microwave type sensor.

18. The UVC germicidal illumination device according to claim 1, wherein said relay is an electro-magnetic SPST type relay.

19. The UVC germicidal illumination device according to claim 1, wherein said relay is a solid-state SPST type relay.

20. The UVC germicidal illumination device according to claim 1, wherein said relay is a low-voltage reed SPST type relay.

21. The UVC germicidal illumination device according to claim 1, wherein said relay is an electro-magnetic SPDT type relay.

22. The UVC germicidal illumination device according to claim 1, wherein said relay is a solid-state SPDT type relay.

23. The UVC germicidal illumination device according to claim 1, wherein said relay is a low-voltage reed SPDT type relay.

24. The UVC germicidal illumination device according to claim 1, wherein said UVC germicidal illumination device is a combination UVC germicidal and white color general lighting illumination device.

25. A UVC germicidal illumination device, comprising:
a power source configured to supply input power to said UVC germicidal illumination device;
at least one UVC light source configured to generate ultraviolet light;
a first at least one power supply unit configured to provide output power to the at least one UVC light source;
a relay connected between said power source and said first at least one power supply unit;
at least one sensor that is in communication with the relay and configured to generate a sensor output signal responsive to a detection of a person or object by the at least one sensor;
wherein said relay is configured to receive the sensor output signal from the at least one sensor and disconnect the power source from the first at least one power supply unit in response to the received sensor output signal;
wherein said relay is further configured to re-connect the power source to said first at least one power supply unit when said sensor output signal is no longer being received by the relay; and wherein the UVC germicidal illumination device further comprises a second at least one power supply unit providing output power to at least one white color light source;
wherein said relay is triggered by said sensor output signal to turn on said second at least one power supply unit and at least one white color light source via the Normally Open output connection of said relay when said at least one sensor does detect a person or object is entering or already present in a room or space; and
wherein said relay is triggered by said sensor output signal to turn off said second at least one power supply unit and at least one white color light source via the Normally Open output connection of said relay when said at least one sensor does not detect a person or object entering or is already present in a room or space.

26. The UVC germicidal illumination device according to claim 25, wherein said second at least one power supply unit is at least one fluorescent ballast.

27. The UVC germicidal illumination device according to claim 25, wherein said second at least one power supply unit is at least one metal halide ballast.

28. The UVC germicidal illumination device according to claim 25, wherein said second at least one power supply unit is at least one inverter.

29. The UVC germicidal illumination device according to claim 25, wherein said second at least one power supply unit is at least one LED driver.

30. The UVC germicidal illumination device according to claim 25, wherein said at least one white color light source is at least one white color light fluorescent lamp.

31. The UVC germicidal illumination device according to claim 25, wherein said at least one white color light source is at least one white color light HID lamp.

32. The UVC germicidal illumination device according to claim 25, wherein said at least one white color light source is at least one white color light cold cathode lamp.

33. The UVC germicidal illumination device according to claim 25, wherein said at least one white color light source is at least one white color light LED lamp.

34. The UVC germicidal illumination device according to claim 25,
wherein said relay is triggered by said sensor output signal to turn on said second at least one power supply unit and at least one white color light source via a Normally Closed output connection of said relay when said at least one sensor does detect a person or object is entering or already present in a room or space, and
wherein said relay is triggered by said sensor output signal to turn off said second at least one power supply unit and at least one white color light source via the Normally Closed output connection of said relay when said at least one sensor does not detect a person or object entering or is already present in a room or space.

35. A combination UVC germicidal and white color general lighting luminaire comprising:
a source of input power to said combination UVC germicidal and white color general lighting luminaire;
a first at least one power supply unit providing output power to at least one UVC light source;
a second at least one power supply unit providing output power to at least one white color light source;
at least one sensor in communication with a relay;
wherein said relay is triggered by a sensor output signal to turn off said first at least one power supply unit and at least one UVC light source via the Normally Closed output connection of said relay, and turn on said second at least one power supply unit and at least one white color light source via a Normally Open output connection of said relay when said at least one sensor does detect a person or object entering or is already present in a room or space; and
wherein said relay is triggered by said sensor output signal to turn on said first at least one power supply unit and at least one UVC light source via the Normally Closed output connection of said relay, and turn off said second at least one power supply unit and at least one white color light source via the Normally Open output connection of said relay when said at least one sensor does not detect a person or object entering or is already present in a room or space.

36. The combination UVC germicidal and white color general lighting luminaire according to claim 35, wherein said source of input power is AC mains line voltage power.

37. The combination UVC germicidal and white color general lighting luminaire according to claim 35, wherein said source of input power is DC voltage power.

38. The combination UVC germicidal and white color general lighting luminaire according to claim 35, wherein said at least one sensor is at least one PIR type sensor.

39. The combination UVC germicidal and white color general lighting luminaire according to claim 35, wherein said at least one sensor is at least one microwave type sensor.

40. The combination UVC germicidal and white color general lighting luminaire according to claim 35, wherein said at least one sensor is at least one radio-frequency type sensor.

41. The combination UVC germicidal and white color general lighting luminaire according to claim 35, wherein said at least one sensor is at least one ultrasonic type sensor.

42. The combination UVC germicidal and white color general lighting luminaire according to claim 35, wherein said at least one sensor is at least one radar type sensor.

43. The combination UVC germicidal and white color general lighting luminaire according to claim 35, wherein said at least one sensor is a combination of at least one PIR type sensor and at least one microwave type sensor.

44. The combination UVC germicidal and white color general lighting luminaire according to claim 35, wherein said relay is an electro-magnetic SPDT type relay.

45. The combination UVC germicidal and white color general lighting luminaire according to claim 35, wherein said relay is a solid-state SPDT type relay.

46. The combination UVC germicidal and white color general lighting luminaire according to claim 35, wherein said relay is a low-voltage reed SPDT type relay.

47. A combination UVC germicidal and white color general lighting LED lamp comprising:
- a source of input power to said combination UVC germicidal and white color general lighting LED lamp;
- a first at least one LED driver providing output power to at least one UVC LED light source;
- a second at least one LED driver providing output power to at least one white color LED light source;
- at least one sensor in communication with a relay;
- wherein said relay is triggered by a sensor output signal to turn off said first at least one LED driver and at least one UVC LED light source via the Normally Closed output connection of said relay, and turn on said second at least one LED driver and at least one white color LED light source via the Normally Open output connection of said relay when said at least one sensor does detect a person or object entering or is already present in a room or space; and
- wherein said relay is triggered by said sensor output signal to turn on said first at least one LED driver and at least one UVC LED light source via the Normally Closed output connection of said relay, and turn off said second at least one LED driver and at least one white color LED light source via the Normally Open output connection of said relay when said at least one sensor does not detect a person or object entering or is already present in a room or space.

48. The combination UVC germicidal and white color general lighting LED lamp according to claim 47, wherein said source of input power is AC mains line voltage power.

49. The combination UVC germicidal and white color general lighting LED lamp according to claim 47, wherein said source of input power is DC voltage power.

50. The combination UVC germicidal and white color general lighting LED lamp according to claim 47, wherein said at least one sensor is at least one PIR type sensor.

51. The combination UVC germicidal and white color general lighting LED lamp according to claim 47, wherein said at least one sensor is at least one microwave type sensor.

52. The combination UVC germicidal and white color general lighting LED lamp according to claim 47, wherein said at least one sensor is at least one radio-frequency type sensor.

53. The combination UVC germicidal and white color general lighting LED lamp according to claim 47, wherein said at least one sensor is at least one ultrasonic type sensor.

54. The combination UVC germicidal and white color general lighting LED lamp according to claim 47, wherein said at least one sensor is at least one radar type sensor.

55. The combination UVC germicidal and white color general lighting LED lamp according to claim 47, wherein said at least one sensor is a combination of at least one PIR type sensor and at least one microwave type sensor.

56. The combination UVC germicidal and white color general lighting LED lamp according to claim 47, wherein said relay is an electro-magnetic SPDT type relay.

57. The combination UVC germicidal and white color general lighting LED lamp according to claim 47, wherein said relay is a solid-state SPDT type relay.

58. The combination UVC germicidal and white color general lighting LED lamp according to claim 47, wherein said relay is a low-voltage reed SPDT type relay.

* * * * *